(12) United States Patent
Tulkki

(10) Patent No.: US 8,187,195 B2
(45) Date of Patent: May 29, 2012

(54) SENSOR WIRE ASSEMBLY

(75) Inventor: Sauli Tulkki, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1345 days.

(21) Appl. No.: 11/247,598

(22) Filed: Oct. 12, 2005

(65) Prior Publication Data

US 2007/0106165 A1    May 10, 2007

(51) Int. Cl.
*A61B 5/02* (2006.01)
(52) U.S. Cl. .................................. 600/486; 600/585
(58) Field of Classification Search ............... 600/585, 600/486
See application file for complete search history.

(56) References Cited

U.S. PATENT DOCUMENTS

| | | | |
|---|---|---|---|
| 4,480,488 A | 11/1984 | Read et al. | |
| 4,495,820 A | 1/1985 | Shimada et al. | |
| 5,146,788 A | 9/1992 | Raynes | |
| 5,568,815 A | 10/1996 | Raynes et al. | |
| 6,090,052 A * | 7/2000 | Akerfeldt et al. | 600/585 |
| 6,167,763 B1 | 1/2001 | Tenerz et al. | |
| 6,585,660 B2 | 7/2003 | Dorando et al. | |
| 6,615,067 B2 | 9/2003 | Hoek et al. | |
| 6,714,809 B2 * | 3/2004 | Lee et al. | 600/423 |
| 6,878,013 B1 * | 4/2005 | Behan | 439/668 |
| 7,317,409 B2 | 1/2008 | Conero | |
| 2002/0013527 A1 | 1/2002 | Hoek et al. | |
| 2004/0082866 A1 * | 4/2004 | Mott et al. | 600/486 |
| 2005/0054905 A1 * | 3/2005 | Corl et al. | 600/309 |
| 2005/0055244 A1 * | 3/2005 | Mullan et al. | 705/2 |

FOREIGN PATENT DOCUMENTS

| | | |
|---|---|---|
| EP | 0 230 084 A1 | 7/1987 |
| EP | 0973438 (B1) | 11/2003 |
| JP | 62-229882 A | 10/1987 |
| JP | 4-265831 (A) | 9/1992 |
| JP | 8-299286 (A) | 11/1996 |
| JP | 2001-517993 (A) | 10/2001 |
| JP | 2004-528920 (A) | 9/2004 |
| JP | 2005-516230 (A) | 6/2005 |
| WO | WO 2005/012817 (A2) | 2/2005 |

OTHER PUBLICATIONS

Burr-Brown Products "Voltage Output Programmable Sensor Conditioner" PGA309.*

(Continued)

*Primary Examiner* — Max Hindenburg
*Assistant Examiner* — Renee Danega
(74) *Attorney, Agent, or Firm* — Foley & Lardner LLP

(57) ABSTRACT

Sensor wire assembly for measuring a physiological variable in a body, said assembly comprises a sensor element for measuring the physiological variable and to generate a sensor signal in response of said variable, and a guide wire having said sensor element at its distal end, and adapted to be inserted into the body in order to position the sensor element within the body. The assembly further comprises a sensor signal adapting circuitry, being an integrated part of said assembly, wherein the sensor signal is applied to the adapting circuitry that is adapted to automatically generate an output signal, related to the sensor signal, in a standardized format such that the measured physiological variable is retrievable by an external physiology monitor.

18 Claims, 4 Drawing Sheets

OTHER PUBLICATIONS

Photograph of Sentron Angiographic Catheter, circa 1980, showing EEPROM in the connector, 1 pg.
Photograph of Millar VPM-10 catheter connector, supplied to Codman & Shurtleff as OEM equipment, 1 pg.
Endosomatic Systems, Inc., Multichannel Biotelemetry System for Advanced Cardiovascular Hemodynamic Measurements, product brochure, 4 pgs.
Patent Protest of Jun. 12, 2007 by Huntly D. Millar, 4 pgs.

* cited by examiner

SENSOR WIRE ASSEMBLY

FIELD OF THE INVENTION

The present invention relates to a sensor wire assembly for measuring a physiological variable in a body.

BACKGROUND OF THE INVENTION

In many medical procedures, medical personnel need to monitor various physiological conditions that are present within a body cavity of a patient. These physiological conditions are typically physical in nature—such as pressure, temperature, rate-of-fluid flow—and provide the physician or medical technician with critical information as to the status of a patient's condition. Obviously, the manner by which these types of parameters are measured and monitored must be safe, accurate and reliable.

One device that is widely used to monitor such conditions is the blood pressure transducer. A blood pressure transducer senses the magnitude of a patient's blood pressure, and converts it into a representative electrical signal. This electrical signal is then supplied to a vital signs monitor that displays, records or otherwise monitors the magnitude of the patient's blood pressure.

Traditionally, a blood pressure transducer has consisted of a pressure responsive diaphragm that is mechanically coupled to piezoresistive elements connected in a Wheatstone Bridge-type circuit arrangement. When the diaphragm is placed in fluid communication with a body cavity (such as within the arterial or venous system), pressure induced deflections of the diaphragm cause the resistive elements to be stretched (or compressed, depending on their orientation). According to well-known principles, this alters the resistance of the elements in a manner that is proportional to the applied pressure. The magnitude of the applied pressure can thus be detected by applying an excitation power signal (usually in the form of a voltage) to the inputs of the Wheatstone bridge circuit, and by simultaneously monitoring the bridge output signal. The magnitude of that signal reflects the amount by which the bridge resistance has changed, according to Ohm's law.

Typically, an electrical cable connects the Wheatstone bridge portion of the transducer sensor to a transducer amplifier circuit contained within the vital signs monitor. This amplifier circuit supplies the excitation power signal to the Wheatstone bridge, and simultaneously monitors the bridge output signal. The excitation power signal is typically in the form of a voltage and, depending on the monitor type and manufacturer, can have varying magnitudes and formats, both time-varying (sinusoidal, square-waved and pulsed) and time independent (DC).

According to the principles under which conventional Wheatstone-bridge transducers operate, transducer amplifier circuits in most patient monitors have been designed to expect a sensor output signal having a magnitude that is proportional to the magnitude of the excitation power signal and also proportional to the magnitude of the sensed pressure. Because different monitors supply excitation power signals having different magnitudes and/or frequencies, standard proportionality constants have been developed. These proportionality standards allow any sensor to be readily adapted for use with any patient monitor also calibrated to adhere to the proportionality standard.

Several benefits are provided by this compatibility. Blood pressure transducers could be used interchangeably with patient monitors from different manufacturers. As such, medical personnel were not required to select a specific transducer for use with a specific monitor. Further, hospital investments in pre-existing patient monitors were preserved, thereby reducing costs. As a consequence, vital signs monitors adhering to these proportionality standards have achieved almost universal acceptance in medical environments.

However, the blood pressure transducers and monitors that have been previously used, and the resulting standards that have evolved, are not without drawbacks. For instance, the sensors used in these systems were typically positioned external to the patient's body and placed in fluid communication with the body cavity via a fluid-filled catheter line. Pressure variations within the body cavity are then indirectly communicated to the diaphragm by way of fluid contained with the catheter line. As such, the accuracy of such systems has suffered due to variations in hydrostatic pressure and other inconsistencies associated with the fluid column.

In response to this problem, miniaturized sensors using advanced semiconductor technologies have been developed. These types of transducer sensors are extremely accurate, inexpensive and still utilize the well known Wheatstone bridge-type of circuit arrangement, which typically, at least partly, is fabricated directly on a silicone diaphragm. Further, the sensors are sufficiently small such that they can actually be placed on the tip of an indwelling guide wire and reside directly within the arteries, tissues or organs of the patient. This eliminates the need for a fluid line because the fluid pressure is communicated directly to the transducer diaphragm. As a result, these sensors—often referred to as an indwelling or guide wire-tipped transducers—provide a much more accurate measurement of the patient's blood pressure.

Unfortunately, the electrical configurations of these miniaturized semiconductor sensors are not always compatible with the transducer amplifiers in existing patient monitors. For instance, the miniaturized sensors often cannot operate over the entire range of excitation signal magnitudes and frequencies found among the various types of patient monitors. Thus, they cannot be connected directly to many of the patient monitors already in use. To be used with such existing monitors, a specialized interface must be placed between the sensor and the monitor. Such an arrangement necessitates additional circuitry on the interface and, because existing monitors have been designed to provide only limited amounts of power, the additional circuitry may require an independent source of electrical power. As a consequence, use of the newer miniaturized sensors often adds cost and complexity to the overall system.

In addition, because of the above limitations, these sensors must often be configured to generate an output signal which is proportional to the pressure sensed, but that is not related to the excitation signal, supplied to the sensor by the monitor, in a way that is directly usable by the physiology monitor, e.g. the sensitivity may be different. As discussed, this does not conform with the electrical format required by the many monitors that are commercially available and already in widespread use. As such, the newer sensors can only be used with specific monitor types, thereby requiring additional, and often redundant, equipment to be purchased. This is especially undesirable given the cost sensitivities so prevalent in today's health care environment.

U.S. Pat. No. 5,568,815 discloses an interface circuit for interfacing a sensor to a patient monitor. The interface circuit includes a power supply circuit that receives an excitation power signal generated by the patient monitor, and derives therefrom unregulated and regulated supply voltages for use by the electrical components on the interface circuit. Further, the power supply circuit generates an appropriate sensor excitation signal. The interface circuit further includes receiving circuitry for receiving a sensor output signal generated by the sensor. A scaling circuit then scales that signal into a parameter signal that is proportional to the physiological condition detected by the sensor, and that is also proportional to the excitation power signal generated by the patient monitor.

An obvious drawback of the device of U.S. Pat. No. 5,568,815 is that, in order to connect the sensor to the monitor, a separate additional unit in the form of the interface circuit is required.

A similar solution is disclosed in U.S. Pat. No. 6,585,660 that relates to a signal conditioning device that interfaces a variety of sensor devices, such as guide wire-mounted pressure sensors, to physiology monitors. The signal conditioning device includes a processor for controlling a sensor excitation and signal conditioning circuitry within the signal conditioning device. The processor also supplies signals to an output stage on the signal conditioning device representative of processed sensor signals received by a sensor interface of the signal conditioning device. Power for the signal conditioning device processor is supplied by an excitation signal received from a physiology monitor that drives the output stage. In addition, a temperature compensating current source provides an adjustment current to at least one of a pair of resistive sensor elements to compensate for differences between temperature change upon the pair of resistive sensor elements, thereby facilitating nullifying temperature effects upon the resistive sensor elements.

The Association for the Advancement of Medical Instrumentation ("AAMI") has defined power requirements for physiology monitors and in particular the input/output connector to a sensor wire assembly must comply with the standard set by American National Standards Institute ("ANSI")/AAMI BP22-1994 (referred to as "BP22" in the following).

According to the BP22-standard an input/output connector arranged at the proximal end of a five line connector cable includes a pair of differential output signal lines. The output signal lines are driven by a sensor adapting circuitry's output digital to analog converters (discussed further herein below). The differential output signal, by way of example, operates at 5 µV/mmHg/$V_{EXC}$. An operation range of −150 µV/V to 1650 µV/V therefore represents a sensed pressure range of −30 to 330 mmHg. An exemplary resolution (minimum step) for the differential output signal is 0.2 mmHg.

Obvious drawbacks of the available prior art interface devices are that they are bulky and require user input which further increase the complexity of the equipment used in an intensive care operating room.

Furthermore, available interface devices require regular service, calibration, updating of software etc. which increase the logistic administration of the equipment and require a number of extra devices to be used when some of the devices are at service, which all together increase the cost.

The general object of the present invention is to achieve an easy to use sensor wire assembly that reduces the overall cost of handling the assembly.

SUMMARY OF THE INVENTION

The above-mentioned object is achieved by the present invention.

Thus, a sensor wire assembly according to the present invention is directly connectable to a standard input/output connector of a physiology monitor, i.e. obviating the need of an additional interface device which is necessary in the described prior art.

By a standard input/output connector is meant in accordance with an established standard or in accordance with relevant parts of an established standard, e.g. BP22.

The present invention is based on the in-sight that available prior art interface devices are too bulky and sometimes difficult to use.

In the solution disclosed in accordance with the present invention the necessary circuitry is drastically scaled-down in order to be integrated within the socket connector, in the wire connector, or elsewhere along the sensor wire assembly.

The inventor has realized that by using now available standard circuitry, e.g. as signal conditioner unit, the cost for the assembly may be drastically decreased which is a presumption for making the sensor wire assembly a disposable device, i.e. this is due to the fact that the need for service, calibration and software updating, as in the prior art interface devices, have been obviated for the sensor wire assembly according to the present invention.

Thus, according to the present invention there is provided a sensor signal adapting circuitry between an intravascular guide wire-mounted pressure sensor and a physiology monitor that displays a human-readable output corresponding to the sensed pressure. The adapting circuitry receives synchronization information, e.g. in the form of an excitation signal, from the physiology monitor and provides conditioned, standardized output in the form of an analog voltage output signal.

According to a preferred embodiment the adapting circuitry energizes the guide wire-mounted pressure sensor, e.g. with a sensor current/voltage, conditions a sensed analog sensor input signal, and performs mathematical transformations (by means of a microprocessor) to render the standardized output to the physiology monitor.

Furthermore, major advantages of the present invention is that no user input is required in order to use the assembly, instead it is ready to plug-in and directly use and that the sensor signal adapting circuitry automatically adapts the output to the applied sensor signal.

SHORT DESCRIPTION OF THE APPENDED DRAWINGS

Preferred embodiments of the present invention will be described in detail in the following with reference made to accompanying drawings, in which:

FIG. 1 shows an exemplifying sensor mounted on a guide wire in accordance with prior art and which is applicable herein.

FIG. 2 schematically illustrates a sensor wire assembly for measuring a physiological variable in a body according to the present invention.

DETAILED DESCRIPTION OF PREFERRED EMBODIMENTS OF THE INVENTION

In the prior art, it is known to mount a sensor on a guide wire and to position the sensor via the guide wire in a blood vessel in a living body to detect a physical parameter, such as pressure or temperature. The sensor includes elements that are directly or indirectly sensitive to the parameter. Numerous patents describing different types of sensors for measuring physiological parameters are owned by the applicant of the present patent application. For example, temperature could be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure.

In order to power the sensor and to communicate signals representing the measured physiological variable to an external physiology monitor, one or more cables or leads for transmitting the signals are connected to the sensor, and are routed along the guide wire to be passed out from the vessel to the external physiology monitor via a connector means. In addition, the guide wire is typically provided with a central metal wire (core wire) serving as a support for the sensor and (optionally) also as an electrical connection to the sensor, and a surrounding tubing. Hence, a guide wire typically comprises a core wire, leads and a protective tubing.

Figure 1:
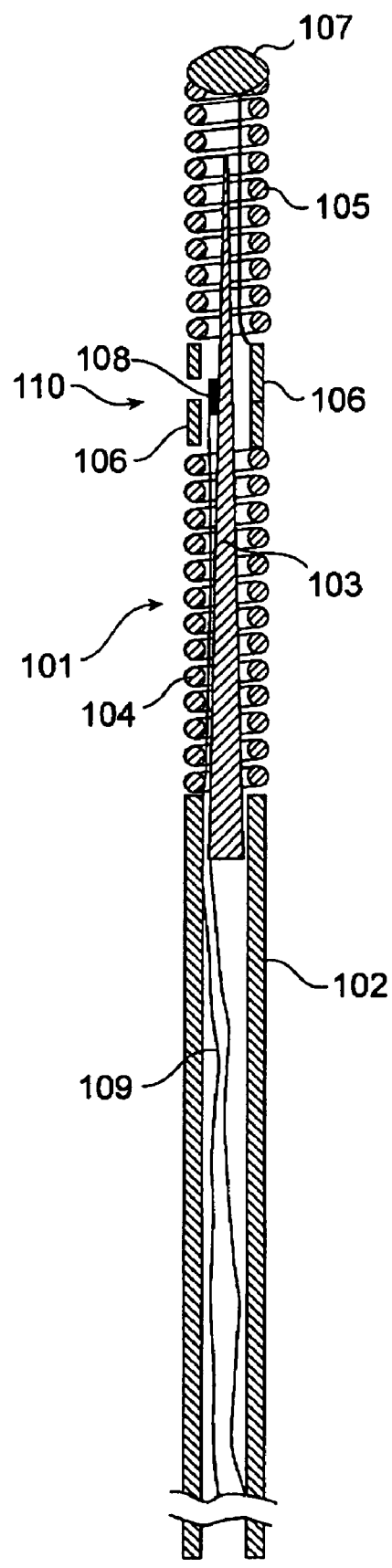

FIG. 1 shows an exemplifying sensor mounted on a guide wire in accordance with conventional design which is applicable for the present invention. The sensor guide wire 101 comprises a hollow tube 102, a core wire 103, a first spiral portion 104, a second spiral portion 105, a jacket or sleeve 106, a dome-shaped tip 107, a sensor element or chip 108, and one or several electrical leads 109. The tube 102 has typically been treated to give the sensor guide construction a smooth outer surface with low friction. The proximal end of the first spiral portion 104 is attached to the distal end of the hollow tube 102, while the distal end of the first spiral portion 104 is attached to the proximal end of the jacket 106. The proximal end of the second spiral portion 105 is connected to the distal end of the jacket 106, and the dome-shaped tip 107 is attached to the distal end of the second spiral portion 105. The core wire 103 is at least partly disposed inside the hollow tube 102 such that the distal portion of the core wire 103 extends out of the hollow tube 102 and into the second spiral portion 105. The sensor element 108 is mounted on the core wire 103 at the position of the jacket 106, and is connected to an external physiology monitor (not shown in the FIG. 1) via the electrical leads 109. The sensor element 108 comprises a pressure sensitive device in the form of a membrane (not shown in the FIG. 1), which through an aperture 110 in the jacket 106 is in contact with a medium, such as blood, surrounding the distal portion of the sensor guide wire 101.

Figure 2:
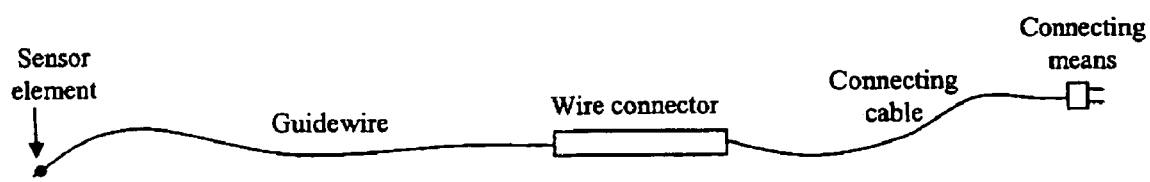
Figure 3:
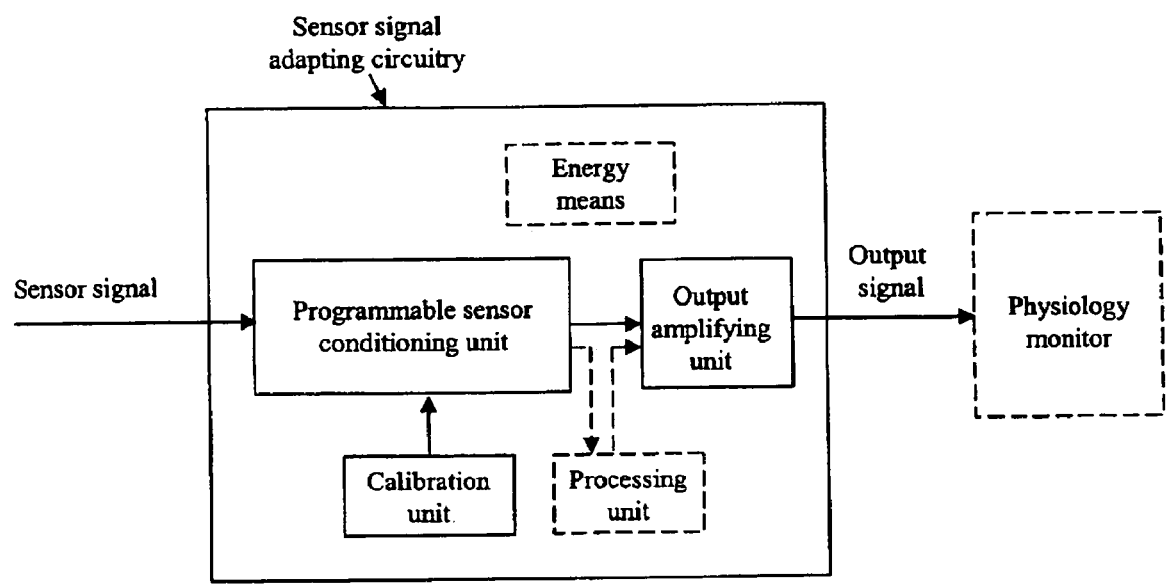
FIG. 3 shows a block diagram schematically illustrating a sensor signal adapting circuitry according to the present invention.

FIG. 2 schematically illustrates a sensor wire assembly for measuring a physiological variable in a body according to the present invention, and FIG. 3 shows a block diagram schematically illustrating a sensor signal adapting circuitry according to the present invention.

With references to FIGS. 2 and 3 the assembly comprises a sensor element for measuring the physiological variable and to generate a sensor signal in response of said variable, a guide wire having said sensor element at its distal portion, preferably close to its distal end, and adapted to be inserted into the body in order to position the sensor element within the body. The assembly further comprises a sensor signal adapting circuitry (FIG. 3), being an integrated part of the assembly, wherein the sensor signal is applied to the adapting circuitry that is adapted to automatically generate an output signal, related to the sensor signal, in a format such that the measured physiological variable is retrievable by an external physiology monitor. The sensor signal adapting circuitry comprises a programmable sensor conditioning unit, a calibration unit, being a storage means into which calibration data may be supplied, stored and altered, e.g. an electrically erasable programmable read-only memory (EEPROM), energy means and an output amplifying unit.

The programmable sensor conditioning unit is preferably a PGA309 programmable analog sensor conditioner (available from Texas Instruments Inc.) specifically designed for bridge sensors.

Also illustrated in FIG. 2 is a connecting means to connect the assembly to an input/output connector of the physiology monitor.

The assembly further comprises a connector cable connected to the guide wire via a wire connector arranged at said connecting cable, where the guide wire is arranged at the distal part of the assembly. The adapting circuitry is preferably arranged in the wire connector but may also be arranged in the connecting means or elsewhere along the assembly.

Figure 4:
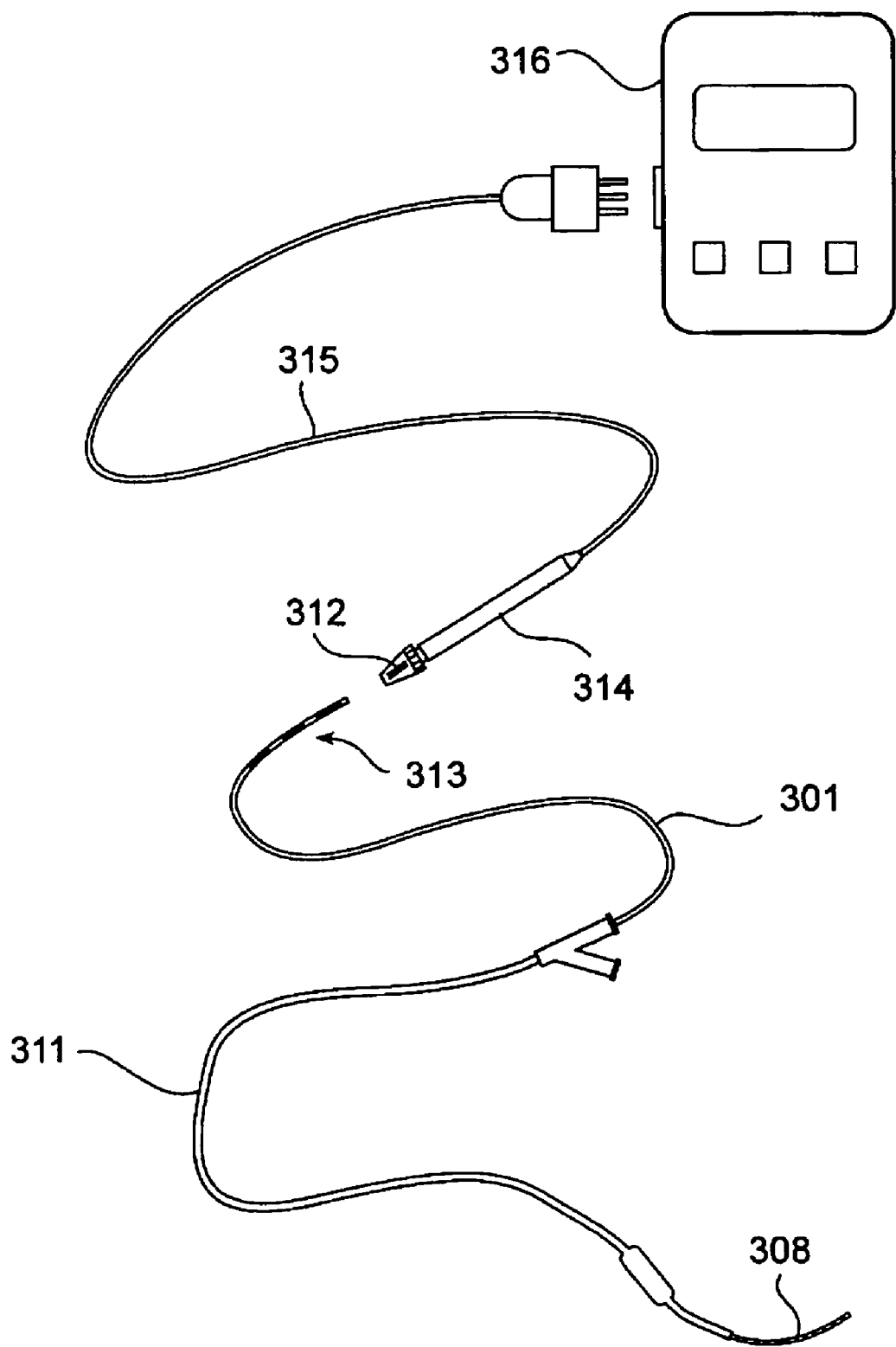
FIG. 4 shows a block diagram illustrating a sensor assembly in accordance with a preferred embodiment of the present invention.

FIG. 4 shows a sensor wire assembly in accordance with a preferred embodiment of the present invention comprising a sensor element 308 mounted on a guide wire 301, whose distal end is provided with a male connector 313. The sensor assembly further comprises a sensor signal adapting circuitry 312 for adapting a format of the sensor element signal representing the measured physiological variable, and also comprises a wire connector in the form of a female connector 314 provided at one end of a connecting cable 315. In this particular embodiment, the signal adapting circuitry 312 is arranged to be located at the female connector 314. However, the adapting circuitry may be located virtually anywhere along the sensor assembly, as long as it is an integral part of the sensor assembly. In use, the sensor assembly is connected via its male connector 313 to the female connector 314 provided at one end of the interface connector cable 315. The male connector 313 and the female connector 314 together form the wire connector illustrated in FIG. 2. The other end of the cable is provided with a plug-in contact for connection to a physiology monitor 316 on which values representing the pressure measured by the sensor element 308 can be displayed.

Also shown in FIG. 4 is a balloon catheter 311, which has been threaded onto the guide wire 301 after a physician has placed the guide wire in an appropriate location in the body. This is achieved by disconnecting the male connector 313 of the guide wire from the female connector 314 of the connector cable 315, and passing the balloon catheter 311 over the guide wire. When the balloon catheter is properly located, the guide wire can again be connected to the interface cable for further measurements.

The physiology monitor 316 supplies the sensor assembly with a reference voltage via the cable 315. By considering the signal standard with which the physiology monitor 316 complies, which is indicated to the sensor assembly by means of the reference voltage, and the actual value of the physical parameter measured by the sensor element 308, the signal adapting circuitry 312 will process the signal from the sensor element such that an adapted signal in accordance with the standard expected by the monitor may be sent back via the cable 315.

Figure 5:
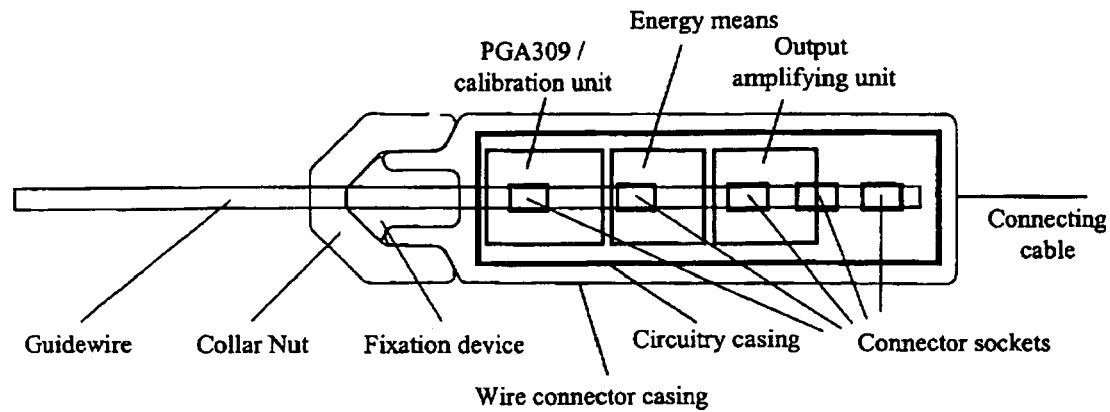
FIGS. 5 and 6 show the wire connector according to a preferred embodiment of the present invention, in FIG. 5 the connector is in an assembled state and in FIG. 6 in a disassembled state.
Figure 6:
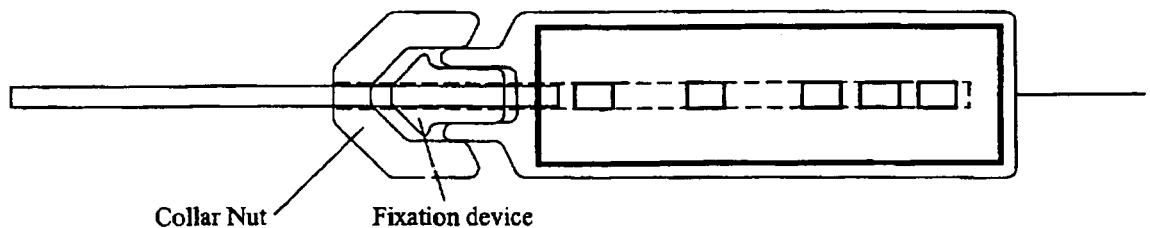

FIGS. 5 and 6 show the wire connector according to a preferred embodiment of the present invention, in FIG. 5 the connector is in an assembled state and in FIG. 6 in a disassembled state.

The wire connector comprises a wire connector casing being the body of a female connector enclosing a circuitry casing that in turn encloses the programmable sensor conditioning unit (PGA309), the calibration unit, e.g. an electrically erasable programmable read-only memory (EEPROM), energy means and the output amplifying unit connecting the adapting circuitry to the connecting cable. The wire connector is provided with a guidewire receptacle tubing in which the guidewire is insertable. A number of connector sockets are arranged along the tubing to be electrically connected to electrical connection points along the inserted part of the guidewire. The connection points are connected to the above-mentioned electrical leads in the hollow tube of the guidewire. The guidewire is inserted into the receptacle tubing and then fixated by means of a fixation device and a collar nut.

As mentioned above the programmable sensor conditioner unit is preferably implemented by means of a PGA309 programmable analog sensor conditioner schematically shown in FIG. 4. The PGA309 is particularly designed for resistive bridge sensor applications and contains three main gain blocks for scaling differential input bridge sensor signals. Hence, as discussed in the above, a signal representing the measured physiological variable may be adapted such that a signal in a format expected by the monitor is provided. This signal format is determined by the reference voltage supplied to the sensor assembly and the actual value of the signal measured by the sensor. The PGA309 can be configured for use with an internal or external voltage reference. In this particular example, an external reference voltage of +5V is supplied to the PGA309.

Thus, the conditioner unit generates an analog output voltage signal related to the sensor signal such that the measured physiological variable may be retrieved by the physiological monitor.

Since each sensor element is an individual item with its own characteristics, each sensor assembly comprises a calibration unit, preferably an electrically erasable programmable read-only memory (EEPROM) which contains individual calibration data obtained during calibration of the sensor element performed for each individual sensor wire assembly. The calibration is performed in connection with manufacture of the sensor wire assembly. Calibration data takes into account parameters such as voltage offsets and temperature drift, etc.

The bridge pressure sensor is preferably energized from the PGA309 via an excitation voltage $V_{EXC}$, generated by the PGA309 circuit. As an alternative the pressure sensor may be energized from a separate energy source, e.g. a battery or a capacitor means.

The PGA309 circuit is energized either from a separate energy source, e.g. a battery or a capacitor, which may be the same energy source that energizes the sensor, or a separate one, or via energy received from the physiology monitor or from a combination of energy sources. The energy source may be charged via the excitation voltage.

For a given excitation voltage $V_{EXC}$, e.g. generated by the PGA309 circuit, the output voltage ($V_{IN1}$-$V_{IN2}$) of the bridge is a voltage proportional to the pressure applied to the sensor. Hence, the sensor output voltage ($V_{IN1}$-$V_{IN2}$) (sensor signal in FIG. 3) of the bridge is proportional to the pressure applied to the sensor, which for a given pressure will vary with the applied excitation voltage. This sensor output voltage is preferably compensated for temperature variation at the site of the sensor and is applied to the PGA309 circuit. The PGA309 circuit also includes gain blocks for adjusting the output signal from that circuit and used in addition to the output amplifying unit mentioned above.

According to another preferred embodiment a processing unit, preferably a microprocessor (e.g. a PIC16C770, shown with dashed lines in FIG. 3) may further be employed to process and adapt the analog output voltage $V_{OUT}$ of the conditioned sensor, which output voltage is supplied via the PGA309 programmable analog sensor conditioner. The analog output signal from the PGA309 circuit is A/D-converted prior it is applied to the processing unit. To adapt the sensor signal to the BP22 signal standard, it may be necessary to process the sensor signal further before it is applied to the physiology monitor. For instance a multiplying digital-analog converter (DAC) which possibly is comprised in the processing unit is supplied With digital data (e.g. a 12-bit word) representing the signal measured by the sensor element and the reference voltage. The resulting product is sent (after having been filtered) to the monitor and is proportional to the measured sensor signal and the reference voltage.

Figure 7:
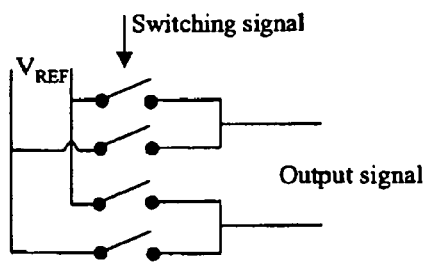
FIG. 7 shows a simplified illustration of a circuitry where the sensor signal is adapted to the BP22 standard (or relevant parts thereof) using pulse width modulation.

If pulse width modulation is required, the circuitry illustrated in the schematic drawing of FIG. 7 may be employed. Here, the signal representing the measured variable is used to create a pulse train by switching the reference voltage $V_{REF}$ according to a switching signal from the processing unit. The pulse train will be filtered, and the resulting voltage is a function of the measured signal and the reference voltage.

The sensor wire assembly may be directly connected to the physiology monitor via the connecting means. In some cases the pin configuration of the connecting means does not fit with the receptacle of the physiology monitor, in those cases an adapter is provided to be connected between the connecting means and the physiology-monitor. The adapter may be a single unit or may include a cable interconnecting the two parts of the adapter, one that fits with the connecting means and another to be connected to the physiology monitor.

According to an alternative embodiment the communication between the sensor wire assembly and the physiology monitor is wireless. This is achieved by integrating a wireless communication unit (not shown) in the assembly, e.g. into a modified wire connector, in order to establish a wireless communication connection by using an established communication protocol, e.g. Bluetooth, to the external physiology monitor.

The sensor wire assembly according to the present invention is adapted to be sterilized prior usage.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor wire assembly for measuring a physiological variable in a body, said assembly comprising:
   a sensor element configured to measure the physiological variable and to generate a sensor signal representative of said variable;
   a guide wire having said sensor element at its distal portion, and adapted to be inserted into the body in order to position the sensor element within the body;
   a wire connector provided with a guide wire receptacle tubing in which a proximal end of said guide wire is inserted, wherein a number of connector sockets are arranged along the tubing to be electrically connected to electrical connection points along an inserted part of the guide wire; and
   a connecting cable configured to directly connect said wire connector to an external physiology monitor,
   wherein the wire connector comprises a wire connector casing that encloses sensor signal adapting circuitry,
   wherein the sensor signal adapting circuitry comprises a programmable sensor conditioning unit, a calibration unit, an energy device, and an output amplifying unit, wherein the assembly is configured such that the sensor signal is provided to the sensor signal adapting circuitry, which is adapted to automatically generate an output signal, related to the sensor signal, in a standardized format such that the measured physiological variable is retrievable by said external physiology monitor via said connecting cable, and wherein the wire connector casing is configured such that, in use, all information delivered to and transmitted from the wire connector is conveyed only by the guide wire and the connecting cable.

2. The sensor wire assembly according to claim 1, wherein said programmable sensor conditioning unit is a PGA309 programmable analog sensor conditioner.

3. The sensor wire assembly according to claim 1, wherein said sensor wire assembly further comprises a connecting device at one end of the connecting cable that is configured to directly connect to an input/output connector of the external physiology monitor.

4. The sensor wire assembly according to claim 1 wherein the guide wire is arranged at a distal part of the sensor wire assembly.

5. The sensor wire assembly according to claim 1, wherein said sensor signal adapting circuitry is energized via said physiology monitor.

6. The sensor wire assembly according to claim 1, wherein said sensor element is energized via said sensor signal adapting circuitry.

7. The sensor wire assembly according to claim 6, wherein said sensor element is energized by the energy device of the sensor signal adapting circuitry, wherein the energy device is an integrated part of the sensor wire assembly.

8. The sensor wire assembly according to claim 1, wherein said sensor wire assembly is adapted to be sterilized prior to usage.

9. The sensor wire assembly according to claim 1, wherein said standardized format is a BP22-standard or relevant parts of the BP22-standard.

10. The sensor wire assembly according to claim 1, wherein the calibration unit includes a storage device that contains individual calibration data obtained during calibration of the sensor element, performed for each individual sensor wire assembly, wherein the calibration is performed in connection with manufacture of the sensor wire assembly.

11. The sensor wire assembly according to claim 1, wherein the wire connector casing encloses a circuitry casing that in turn encloses the sensor signal adapting circuitry.

12. The sensor wire assembly according to claim 1, wherein the programmable sensor conditioning unit is a programmable analog sensor conditioner specially designed for bridge sensors.

13. The sensor wire assembly according to claim 1, wherein the sensor element is energized by another energy device that is an integrated part of the sensor wire assembly.

14. The sensor wire assembly according to claim 1, further comprising the external physiology monitor.

15. The sensor wire assembly according to claim 1, wherein the connector sockets of the wire connector are spaced along a longitudinal axis of the tubing of the wire connector.

16. The sensor wire assembly according to claim 1, wherein the sensor signal adapting circuitry is configured to generate the output signal in different formats, each format being compatible with a different type of external physiology monitor.

17. The sensor wire assembly according to claim 1, wherein the sensor signal adapting circuitry is configured to receive synchronization information from the external physiology monitor and in response provide conditioned, standardized output for the external physiology monitor.

18. The sensor wire assembly according to claim 1, wherein the wire connector is physically separate from the external physiology monitor.

* * * * *